US012153201B2

(12) United States Patent
Litsch et al.

(10) Patent No.: US 12,153,201 B2
(45) Date of Patent: Nov. 26, 2024

(54) OPTICAL OBSERVATION SYSTEM WITH A CONTACTLESS POINTER UNIT, OPERATING METHOD AND COMPUTER PROGRAM PRODUCT

(71) Applicant: Carl Zeiss Meditec AG, Jena (DE)

(72) Inventors: Dominik Litsch, Schorndorf (DE); Stefan Saur, Aalen (DE)

(73) Assignee: Carl Zeiss Meditec AG, Jena (DE)

( * ) Notice: Subject to any disclaimer, the term of this patent is extended or adjusted under 35 U.S.C. 154(b) by 966 days.

(21) Appl. No.: 17/107,566

(22) Filed: Nov. 30, 2020

(65) Prior Publication Data

US 2021/0165197 A1 Jun. 3, 2021

(30) Foreign Application Priority Data

Nov. 28, 2019 (DE) ...................... 10 2019 132 308.8

(51) Int. Cl.
*G02B 21/00* (2006.01)
*A61B 34/20* (2016.01)
(Continued)

(52) U.S. Cl.
CPC .......... *G02B 21/0012* (2013.01); *A61B 34/20* (2016.02); *A61B 34/30* (2016.02);
(Continued)

(58) Field of Classification Search
CPC ..... G02B 21/0012; A61B 34/20; A61B 34/30; A61B 2034/2055; A61B 2034/2068;
(Continued)

(56) References Cited

U.S. PATENT DOCUMENTS 9,622,832 B2 4/2017 Birkenbach et al.
2002/0077540 A1* 6/2002 Kienzle, III ....... A61B 17/1703
606/130

(Continued)

FOREIGN PATENT DOCUMENTS

EP         2165671 A1      3/2010
WO   WO-2004070581 A2 *   8/2004 ......... A61B 17/1703
WO       2015/135055 A1   9/2015

OTHER PUBLICATIONS

English translation and Office action of the German Patent Office dated Jul. 23, 2020 in German patent application 10 2019 132 308.8 on which the claim of priority is based.

*Primary Examiner* — Sean D Mattson
(74) *Attorney, Agent, or Firm* — Walter Ottesen, P.A.

(57) ABSTRACT

An optical observation system includes a contactless pointer unit having a real component including a position labeling device and a virtual component including a virtual tip which is at least intermittently spaced apart from the real component. The system includes a unit for capturing at least one portion of an object and a unit for capturing a position and an alignment of the real component and a unit configured to display the captured portion of the object. The system includes a control unit for ascertaining a position of the virtual tip based on the captured position and alignment of the real component and for arranging for the image output unit to display, with a mark, the position of the virtual tip in the displayed captured portion of the object. An operating method, a pointer device suitable as a real component and a computer program product are provided.

18 Claims, 5 Drawing Sheets

(51) Int. Cl.
 *A61B 34/30* (2016.01)
 *A61B 90/00* (2016.01)
(52) U.S. Cl.
 CPC ......... *A61B 2034/2055* (2016.02); *A61B 2034/2068* (2016.02); *A61B 2090/365* (2016.02)
(58) Field of Classification Search
 CPC ...... A61B 2034/2065; A61B 2090/365; A61B 2090/372; A61B 2090/502; A61B 2017/00203; A61B 90/25
 See application file for complete search history.

(56) References Cited

U.S. PATENT DOCUMENTS

| | | | |
|---|---|---|---|
| 2003/0163038 A1 | 8/2003 | Simon et al. | |
| 2011/0069159 A1 | 3/2011 | Soler et al. | |
| 2012/0323364 A1* | 12/2012 | Birkenbach | G06F 3/017 700/257 |
| 2015/0287236 A1* | 10/2015 | Winne | G06T 15/08 382/128 |
| 2016/0310218 A1 | 10/2016 | Ruckel et al. | |
| 2016/0354152 A1* | 12/2016 | Beck | A61B 34/10 |
| 2017/0076501 A1* | 3/2017 | Jagga | G06T 7/73 |
| 2017/0082847 A1* | 3/2017 | Wilzbach | A61B 34/20 |
| 2018/0042681 A1 | 2/2018 | Jagga | |
| 2018/0049622 A1* | 2/2018 | Ryan | A61B 1/0004 |
| 2021/0137632 A1* | 5/2021 | Stopp | A61B 90/20 |

* cited by examiner

OPTICAL OBSERVATION SYSTEM WITH A CONTACTLESS POINTER UNIT, OPERATING METHOD AND COMPUTER PROGRAM PRODUCT

CROSS REFERENCE TO RELATED APPLICATION

This application claims priority of German patent application no. 10 2019 132 308.8, filed Nov. 28, 2019, the entire content of which is incorporated herein by reference.

FIELD OF THE INVENTION

The present disclosure relates to an optical observation system with a contactless pointer unit and to a method for operating such an optical observation system. Moreover, the disclosure relates to a computer program product and to a pointer device with a position labeling device.

BACKGROUND OF THE INVENTION

By way of example, an optical observation system is used in the field of medicine and includes, for example, a microscope, in particular a surgical microscope. In addition to an image recording and image reproduction unit for recording, that is, capturing, an object or portion of an object, for example a patient or an operating region, that is, a site, of a patient in the field of medicine, the optical observation system can also provide, for example, for the image recording unit to be mounted in focusable and alignable fashion and, for example, for the image recording unit to be able to be automatically aligned relative to the portion of the object to be observed via a control unit using a robotic stand in order to provide the best possible view on the region to be observed for the user, for example the best possible view on the site for a surgeon in the case of a surgical microscope. Moreover, modern surgical microscopes provide the option of superimposing additional information into the visual field of the user, for example on a screen, which shows the site, directly in the eyepiece, for example, the binocular tube, of the microscope or into smartglasses for the user.

To control the alignment of the image recording unit and the superimposition of additional information and to place markings, provision in the process can be made for the user to use a pointer device, that is, a pointer unit, that is, a pointer, for example, a pointer stick or any other mechanical pointer means, the position of which, at least that of the end region or of the tip, and the alignment of which are captured by a navigation system which is part of the optical observation system, the navigation system including a position data capture unit to this end, wherein the localized, captured position is then evaluated in order to control the execution of the various functions on the basis thereof. By way of example, a robotic surgical microscope can be aligned or positioned in this way. By way of example, the navigation system can be configured to digitally mark points in the visual field or to mirror medical data, for example, magnetic resonance imaging (MRI) data, into the visual field. To this end, usually the position of the object, that is, the patient, is initially captured by virtue of an antenna being applied to the latter and a one-time referencing of the object or the patient with respect to its/their antenna being carried out via a mechanical pointer device with antenna or a laser pointer. For digital marking or selecting of the superimposition of location by the user, the physical, mechanical tip of the pointer device is moved into the region of the object, for example, into the site of the patient, to the position of interest, wherein the pointer device may also serve as a probe and/or include further functions.

EP 2 165 671 A1 discloses a surgical instrument which also serves as a pointer instrument for medical navigation. It includes a tip sensor and a transmitter in the handle section.

US 2016 0310 218 A1 discloses a medical observation system, in which the position of a mechanical medical instrument in an operating region, that is, a site, is captured, tracked and presented, with views of regions in the vicinity of the instrument also being presented.

US 2018 0042 681 A1 discloses a medical observation system, in which the position of a mechanical surgical instrument in an operating region is captured and tracked and a virtual representation of the surgical instrument is superimposed into views of the operating region, where waypoints for the instrument can be marked.

U.S. Pat. No. 2,003,163 038 A1 discloses a navigation system for a surgical instrument, in which the three-dimensional perspective on the instrument can be adapted, wherein a three-dimensional representation of the surgical instrument is generated, which is presented in superimposed fashion on image data of the patient.

US 2011 0069 159 A1 discloses a system with which a virtual representation of an object introduced into the patient's body, for example a catheter, can be displayed.

Even if the generation of a virtual representation of whole instruments and pointers is provided in part, real mechanical instruments and pointers are used in the real operating region and so there is actual contact with the patient, as a result of which the biocompatibility of the material of the contact region of the pointer must be ensured, just like the sterility of the pointer, that is, the pointer device or pointer unit.

Moreover, there is a need for great accuracy and stability of the relative position of the pointer, in particular of its tip, relative to the markers, on the basis of which the position is determined. Long pointers, in particular, can cause a significant resultant error, especially angle errors. Moreover, the sterilization process required for medical applications represents a source for changes as a result of mechanical action on the pointer. Therefore, there is a need for time-consuming calibrations by the user and/or for particularly dimensionally stable and precise, and hence expensive, pointers, even if the pointers could be disposable articles depending on the application.

SUMMARY OF THE INVENTION

It is an object of the invention to provide an option allowing an optical observation system to be operated with a pointer device, that is, a pointer, which offers high accuracy and is producible in cost-effective fashion at the same time.

The object can, for example, be achieved by an optical observation system having a contactless pointer unit having a real component and a virtual component, wherein the real component includes at least one position labeling device and the virtual component includes a virtual tip which is at least intermittently spaced apart from the real component; an image recording unit configured to capture at least a portion of an object; a position data capture unit configured to capture a position and an alignment of the real component of the contactless pointer unit; an image output unit configured to display the captured portion of the object; and a control unit configured to ascertain a position of the virtual tip on the basis of the captured position and alignment of the real component of the contactless pointer unit and to cause the image output unit to display the position of the virtual tip with a mark in the displayed captured portion of the object.

The object can, for example, also be achieved by a pointer device for an optical observation system having a contactless pointer unit including a real component and a virtual component, wherein the virtual component includes a virtual tip which is at least intermittently spaced apart from the real component, an image recording unit configured to capture at least a portion of an object, a position data capture unit configured to capture a position and an alignment of the real component of the contactless pointer unit, an image output unit configured to display the captured portion of the object, and a control unit configured to ascertain a position of the virtual tip on the basis of the captured position and alignment of the real component of the contactless pointer unit and to cause the image output unit to display the position of the virtual tip with a mark in the displayed captured portion of the object. The pointer device includes a pointer device body including a labeling device; and, the pointer device is configured to be the real component of the optical observation system.

The object can, for example, also be achieved by a method for operating an optical observation system. The method includes capturing at least a portion of an object using an image recording unit of the optical observation system; introducing a real component of a contactless pointer unit into a field of view of an image recording unit which captures at least the portion of the object, the contactless pointer unit including the real component and a virtual component, wherein the real component comprises at least one position labeling device and the virtual component comprises a virtual tip which is at least intermittently spaced apart from the real component; capturing a position and an alignment of the real component of the contactless pointer unit using a position data capture unit of the optical observation system; displaying the captured portion of the object using an image output unit of the optical observation system; ascertaining a position of the virtual tip on the basis of the captured position and alignment of the real component of the contactless pointer unit using a control unit of the optical observation system; and displaying the position of the virtual tip via a mark in the displayed captured portion of the object using the image output unit.

The object can, for example, further be achieved by a computer program product including computer readable program code for an optical observation system having a contactless pointer unit having a real component and a virtual component, wherein the real component includes at least one position labeling device and the virtual component includes a virtual tip which is at least intermittently spaced apart from the real component, an image recording unit configured to capture at least a portion of an object, a position data capture unit configured to capture a position and an alignment of the real component of the contactless pointer unit, an image output unit configured to display the captured portion of the object, and, a control unit configured to ascertain a position of the virtual tip on the basis of the captured position and alignment of the real component of the contactless pointer unit and to cause the image output unit to display the position of the virtual tip with a mark in the displayed captured portion of the object. The computer program product is configured, when executed by a processor, to cause the optical observation system to carry out the above-mentioned method steps.

According to a first aspect of the invention, an optical observation system includes a contactless pointer unit having a real component and a virtual component, wherein the real component includes at least one position labeling means/labeling device and the virtual component includes a virtual tip which is at least intermittently spaced apart from the real component. Moreover, the optical observation system includes an image recording unit configured to capture at least one portion of an object and a position data capture unit configured to capture a position and an alignment of the real component of the contactless pointer unit and an image output unit configured to display the captured portion of the object. Furthermore, the optical observation system includes a control unit which is configured to ascertain a position of the virtual tip on the basis of the captured position and alignment of the real component of the contactless pointer unit and to arrange for the image output unit to display with a mark the position of the virtual tip in the displayed captured portion of the object.

In contrast to the mechanical, real component of the contactless pointer unit, the virtual component is only defined by the position of its tip relative to the position of the real component, for example by a calculation prescription or an underlying model, which defines this position. The virtual component exists as a result of the fact that the control unit, which is or includes a programmable device having at least a processor and a memory, ascertains the position of the virtual tip by applying a stored calculation prescription. Here, the distance and the relative spatial position of the virtual tip in relation to the position labeling means of the real component of the contactless pointer unit are definable as desired. Thus, the real component represents a pointer device, the tip or working point of which does not correspond to the distal end, that is, the end of the real component furthest away from the hand of the user; instead, the working point thereof, as a virtual tip, is arranged at a distance from the real component at least intermittently, wherein the position and alignment, that is, orientation, of the real component determines the position of the virtual tip which is spaced apart in defined fashion and the position and alignment of the real component is determinable on the basis of its position labeling means.

Here, the term "spaced apart" denotes a distance between the virtual tip and the real component of the contactless pointer unit, which is greater than zero. Here, "at least intermittently spaced apart" includes the fact that provision can be made for the virtual tip not having to be spatially separated from the real component at all times during the operation of the contactless pointer unit. By way of example, provision can be made in one embodiment for the calculation prescription, according to which the position of the virtual tip is ascertained relative to the real component, to be available stored and online, already before the contactless pointer unit is put into operation, while, in another embodiment, the position of the virtual tip is placed at a defined initial position at the start during an initialization phase, for example at the center of the image of the portion of the object recorded by the image recording unit, and the real component can be situated at this or any other position at the start and the desired relationship is set only after the selection by the user, who initially brings the real component into a desired position and alignment, and stored as a calculation prescription.

The control unit arranges for the image output unit to display the position of the virtual tip in the displayed captured portion of the object in marked fashion by virtue of either adapting the corresponding image signals to be displayed by the image output unit or, depending on the employed image output unit, controlling the latter such that it adapts the image signals itself.

The position of the virtual tip is superimposed relative to the coordinate system of the position labeling means in marked fashion, for example represented as an arrow, into the image of the observed portion of the object output by the image output unit. The arrow superimposed into the image is moved by moving the real component of the virtual pointer and the described functions can be carried out by the robotic stand or the control unit or the navigation system.

By way of example, the marked display of the virtual tip can include the latter being represented as an arrow, a colored circle or the end of a stick. In a further embodiment, provision can also be made for the entire virtual component of the contactless pointer unit, including the tip, to be presented as a two-dimensional or three-dimensional representation, for example on the basis of its contour. Even if only the tip is represented as an arrow, provision is made in one embodiment for the latter to be presented in a three-dimensional form for the purposes of improving the impression of depth. By way of example, the real component of the contactless pointer unit can be a stick or a differently formed handle or a glove for the user or a ring for a finger of the user, for example a surgeon, with the position labeling means being mounted thereon.

In one embodiment, provision can also be made for the position labeling means to be defined by the visual form of the real component itself.

By way of example, an image recording unit includes one or more image sensors for capturing, that is, recording, images and image sequences, that is, videos, of at least one portion of an object, for example a body region or operating region, that is, a site, of a patient in the case of a medical observation system. The image recording unit also includes an objective, for example the objective of a microscope.

The position data capture unit is a tracking unit and captures and tracks the position and alignment of the real component of the contactless pointer unit on the basis of the position labeling means. By way of example, if the position labeling means is one or more radio sensors, the position data capture unit can be configured for radio orientation. However, particularly if the position labeling means is an (active or passive) visual position labeling means, the position data capture unit can be connected to the image recording unit or can be realized as a common unit with the latter in order to ascertain the position and alignment of the real component of the contactless pointer unit by image processing methods when the latter is moved in the field of view of the image recording unit. By way of example, if the optical observation system includes a surgical microscope, the position data capture unit can be included by an associated navigation system, for example. Then, the control unit can also be included by the navigation system. In one embodiment, a position data capture unit can also include a dedicated image recording unit itself, explicitly for capturing the real component of the contactless pointer unit in order to ascertain the position and alignment of the pointer unit from the image signal.

By way of example, an image output unit is a monitor, that is, a screen or any other display, smartglasses or, in the case of a microscope, optionally also an eyepiece, for example, a binocular tube, of the microscope.

The optical observation system provides for a contactless pointer unit, that is, a contactless pointer, which cannot come into physical contact with the observed object since the tip only exists virtually. If this relates to a medical observation system, for example a surgical microscope, this renders it possible to avoid having to provide the pointer unit from a biocompatible material, at least in part, and having to take account of the influence of shape changes during handling or cleaning and sterilization, and hence this eliminates a link of the tolerance chain from the position labeling means to the tip of the pointer unit, that is, of the pointer, which can make a new calibration necessary, and so the overall accuracy of the position capture or the tracking is increased, with a cost-effective pointer unit being able to be made available at the same time.

Hence, there are few requirements on the real component of the contactless pointer unit for as long as only the included position labeling means is capturable by the position data capture unit and the position and alignment thereof (and hence also that of the virtual tip) are modifiable according to the needs of the user.

Using the virtual tip also avoids the possibility of the view on the target being concealed by the pointer unit itself. In particular, representations with a free view from the perspective or virtually from the perspective of the pointer unit are possible, even in the case of microscopes.

In one embodiment, provision can be made for a laser beam to be additionally directed at the target of the contactless pointer unit, that is, the position of the virtual tip, in order to draw conclusions about the distance and/or the nature of the surface of the object from the reflection behavior. This additionally ascertained information can additionally be displayed to the user. This offers the advantage of being able to replace information from haptic feedback of a purely mechanical pointer unit, which is also used as a probe, that is otherwise available to the user.

In one embodiment, the position labeling means of the real component of the contactless pointer unit includes a target mark, that is, a visual target which can be unambiguously detected by the position data capture unit. Here, depending on the embodiment, the target mark can consist of one or more parts, depending on whether the alignment in space is also detectable from the nature of the individual target mark or the arrangement of a plurality of parts. This offers the advantage of a cost-effective production and of low requirements in respect of the carrier and the target mark, which, in particular, does not require a power source either. Here, for example, the target mark can be embodied as a sticker or an imprint or in attachable fashion, with the carrier, that is, the real component of the contactless pointer unit, being able to have any desired embodiment. By way of example, the carrier can be a stick, or else a glove or ring on the hand of the user. In a special embodiment, provision can be made for the target mark to be attached directly on the hand of the user, for example the surgeon.

In a further embodiment, provision can alternatively or additionally be made for the position labeling means to include an optical antenna, that is, one or more miniaturized optical signaling devices, wherein the position data capture unit is configured to detect and evaluate the light signals emitted by the optical antenna. By way of example, these can be passive infrared reflectors which reflect infrared rays when irradiated by an external infrared light source. However, this can for example also relate to miniaturized active optical signaling devices, wherein the use of a position labeling means which emits light signals itself can be advantageous, for example, if the illumination should or must otherwise be concentrated in a tight region around the virtual tip and the detection of the target mark outside of this region is unreliable.

In one embodiment, the position labeling means is arranged at a proximal end of the real component of the contactless pointer unit. If the virtual tip represents the (virtual) distal end of the contactless pointer unit, the position labeling means is consequently at a maximum distance from the virtual tip and hence the target or working point of the pointer unit. This provides the best possible view of the target and the region around the latter to the user of the optical observation system, for example the surgeon in the case of a surgical microscope.

In a further embodiment, the position labeling means is provided by the shape of the real component of the contactless pointer unit, that is, the real component of the contactless pointer unit has, overall or in a portion, a characteristic form, the contour of which is detectable by the position data capture unit in recorded images. Here, the detection can be based on the contour alone or can additionally take account of one or more further detectable properties of the real component of the contactless pointer unit, for example the color thereof. To this end, the position data capture unit has information available about the possible shapes of the pointer unit, for example a database with views of the real component of the pointer unit or a three-dimensional model thereof (or of all licensed pointer units).

In one embodiment of the optical observation system, the control unit is configured to ascertain the position of the virtual tip in accordance with a model of the virtual component of the contactless pointer unit, which model is configurable by a user. Here, the model can be configurable in variable fashion and, for example, also be determined by calibration or learning of the virtual tip by the user before the model is stored, for example during an initialization phase and/or also at a later time should the model be intended to be adapted. The model is a calculation prescription and defines how the position and alignment of the real component determines the position and alignment of the virtual component and hence, in particular, of the virtual tip. In one embodiment, the virtual component corresponds to a virtual extension of a real component, which is embodied as a pointer stick. However, provision can also be made for the definition of a more complex shape, for example that of a hook or the like. In one embodiment, provision is made for the length or the shape of the contactless pointer unit to be configured to also be changeable depending on the situation, wherein the change can be set in advance or else be able to be implemented during use by the user, for example by virtue of the virtual tip being defined in the image center in the case of an activation and an identified position labeling means and being displaced therefrom to a target pose by subsequent movements of the real component of the contactless pointer unit. In one embodiment, provision is moreover made for the superimposition and masking of the marking of the position of the virtual tip to be configured to be switchable, for example by an assigned voice command, a foot switch or an option for concealing and showing the position labeling means.

In one embodiment, the control unit is moreover configured to arrange for the image output unit to display selected points and/or regions in the displayed captured portion of the object, in marked fashion and/or with assigned additional information, on the basis of the ascertained position of the virtual tip.

By way of example, additional information can relate to different recordings, for example superimpositions of associated MRI data, x-ray images or the like. Here, provision can be made for these to be superimposed in regions marked by the tip, for the purposes of which a selection function is assigned to the tip, via which, for example, the user can explicitly mark certain positions. By way of example, the selection input can be implemented by a voice command or a hand or foot switch.

In an embodiment, the additional information includes topography information of the object at least in a region around the ascertained position of the virtual tip. This offers the advantage that the virtual tip can be displayed in a manner adapted to the topography of the observed object; in particular, provision can be made in preferred embodiments for a virtual penetration of the virtual tip into the object to lead to a masking of the position marking of the virtual tip or visual highlighting, for example, as a result of a color change.

In an embodiment, the optical observation system includes a microscope, in particular a surgical microscope. In this case, the object is a patient and the portion of the object is an operating region on or in the patient. Then, typically, the user is a physician, in particular a surgeon. On account of the requirements in respect of accuracy and in respect of sterility and biocompatibility, for example, the ability to use a contactless pointer unit is particularly advantageous in the case of surgical microscopes.

In one embodiment, the image output unit includes an eyepiece of the microscope and the control device is configured to arrange for the position of the virtual tip to be a data overlay visible in the eyepiece and/or the image output unit includes a screen and the control device is configured to arrange for the position of the virtual tip to be an overlay of the portion of the object marked on the screen. That is, instead of or in addition to an output, for example by way of a screen on which the virtual tip is digitally overlaid in marked fashion on the recorded portion of the object, that is, for example, the site of the patient, or represented in fused fashion with the latter, the image output unit can include an eyepiece of the microscope and the control device is then configured to arrange for the position of the virtual tip to be a data overlay visible in the eyepiece. Here, an eyepiece refers to an optical eyepiece, for example, through a binocular tube, or a digital eyepiece, for example, image sensor chips.

In an embodiment, the microscope is automatically alignable and includes an alignment control apparatus and the control unit is moreover configured to arrange for the alignment control apparatus to align the microscope on the basis of the position of the virtual tip (align-to-tool function or center-to-tip function). By way of example, this includes an alignment or focusing on the virtual tip. In the case of an automatic alignment, computer-controlled motors, for example, automatically move the microscope or a robotic stand of the microscope. There is an automatic movement of at least one objective lens during automatic focusing.

In a further embodiment, provision is additionally made for the position data capture unit to be configured to continuously update the captured position and alignment of the real component of the contactless pointer unit and for the control unit to be configured to continuously update the ascertained position of the virtual tip and to arrange for the image output unit to continuously update the image output. Consequently, the optical observation apparatus is operable in a live mode, with the term "continuously" including the updates being implemented at least at such short intervals that the impression of an interruption-free video representation arises for the user. The continuous update can also relate to further functions, for example, the alignment of the image recording unit.

According to a second aspect of the invention, a pointer device includes a position labeling means and is configured for use as a real component of a contactless pointer unit of an optical observation system according to any one of the embodiments described above. In this way, the advantages and peculiarities of the optical observation system are also implemented within the scope of a suitable pointer device. Here, the pointer device includes position labeling means on a carrier, or else without a carrier, for example target marks applied directly to the hand of the user. The position labeling means can also be provided by the form of the pointer device itself.

In an embodiment, the pointer device includes a stick, a glove or a ring for a finger of a user of the optical observation system and the position labeling means is mounted on the stick, the glove or the ring. The use of a glove or ring as a carrier of the position labeling means, in particular, gives the user great freedom for using the hand. Moreover, the production costs of such a pointer device are low.

According to a third aspect, a method for operating an optical observation system, preferably an optical operating system according to the first aspect of the invention, includes capturing at least a portion of an object using an image recording unit of the optical observation system. Moreover, the method includes introducing the real component of a contactless pointer unit into a field of view of an image recording unit which captures at least the portion of the object, the contactless pointer unit having a real component and a virtual component, wherein the real component includes at least one position labeling means and the virtual component includes a virtual tip which is at least intermittently spaced apart from the real component, and capturing a position and an alignment of the real component of the contactless pointer unit using a position data capture unit of the optical observation system. Furthermore, the method includes displaying the captured portion of the object using an image output unit of the optical observation system and ascertaining a position of the virtual tip on the basis of the captured position and alignment of the real component of the contactless pointer unit using a control unit of the optical observation system. Additionally, the method includes displaying, in marked fashion, the position of the virtual tip in the displayed captured portion of the object using the image output unit. In this way, the advantages and peculiarities of the optical observation system, including all of its embodiments, are also implemented within the scope of a suitable operating method. Here, apart from the step of introducing the real component of a contactless pointer unit into a field of view of the image recording unit, in particular, the method can be a computer-implemented method, at least in part, which is executed, at least in part, on a processor of the control unit, for example.

Therefore, according to a fourth aspect of the invention, a computer program product includes commands which, when executed on at least one programmable device of an optical observation system according to the first aspect of the invention, cause such an optical observation system according to the first aspect of the invention to carry out steps of the method according to the third aspect of the invention. In this way, the advantages and peculiarities of the optical observation system, including all of its embodiments, are also implemented within the scope of a computer program product. To this end, the computer program product is provided on a computer-readable storage medium, for example, on which the computer program product is stored.

BRIEF DESCRIPTION OF THE DRAWINGS

The invention will now be described with reference to the drawings wherein.

DESCRIPTION OF THE PREFERRED
EMBODIMENTS OF THE INVENTION

It is understood that other embodiments can be used and structural or logical modifications can be undertaken, without departing from the scope of protection of the present invention. It is understood that the features of the various described embodiments can be combined with one another, provided there is no specific statement to the contrary.

Figure 1:
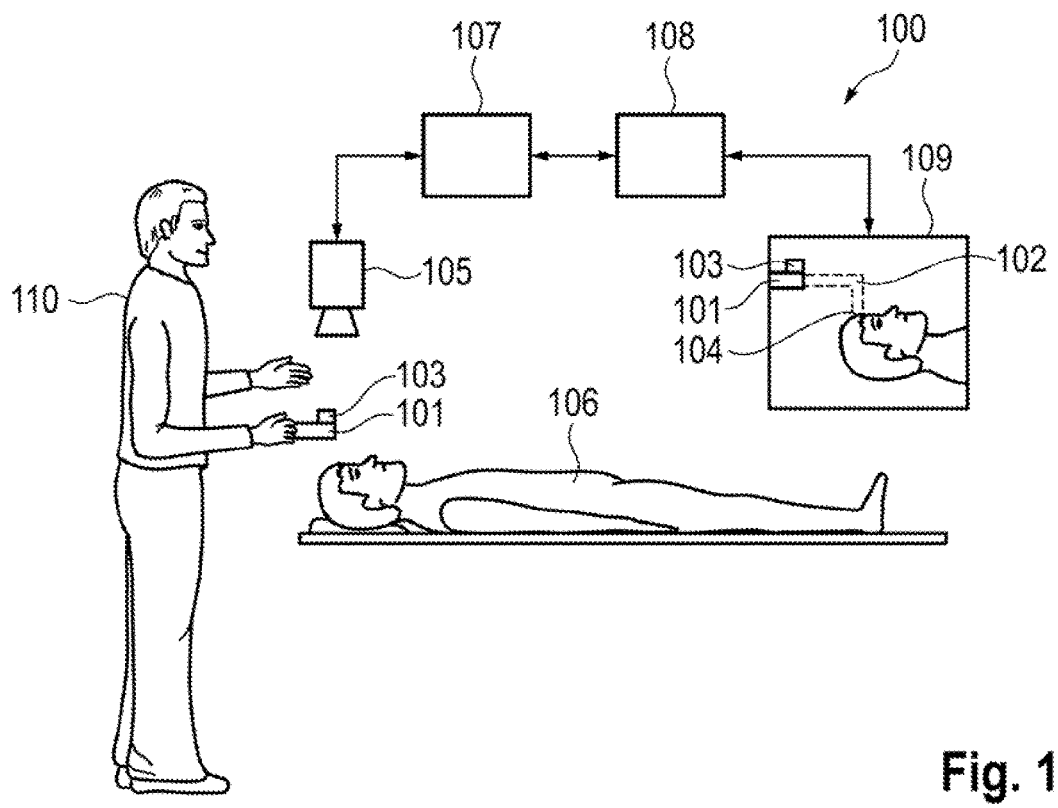
FIG. 1 shows a schematic illustration of an example of an optical observation system according to an embodiment.

FIG. 1 shows a schematic illustration of an example of an optical observation system according to an embodiment. In the shown embodiment, the optical observation system 100 is a medical optical observation system, for example a surgical microscope system. It includes a contactless pointer unit which has a real component 101 and a virtual component 102, wherein the real component 101 includes a position labeling means 103 and the virtual component 102 has a virtual tip 104 which is at least intermittently spaced apart from the real component 101. Here, the real component 101 of the contactless pointer unit is guided by a user 110, for example a surgeon or any other physician, into the observation region, that is, the field of view of an image recording unit 105 which records a portion of an object, the head of a patient 106 including an operating region (not shown) in the shown embodiment. The image recording unit 105, which may consist of one or more individual recording units (inter alia also units that are independent of one another on different stands/systems), captures the portion of the object, that is, for example, an operating region, that is, a site, of the patient 106, together with the real component 101 of the contactless pointer unit and the image recording unit is connected to a position data capture unit 107, which is configured to capture the current position and alignment of the real component 101 of the contactless pointer unit. In the shown embodiment, this is implemented by evaluating the images recorded by the image recording unit 105 using image processing methods, which are carried out on a processor of a programmable device and which detect at least the position labeling means 103, which can be, for example, a stuck-on target mark or an optical antenna, and the position and alignment of the real component 101 of the contactless pointer unit are ascertained on the basis thereof.

The position data capture unit 107 is connected to a control unit 108 which is configured to this end; that is, for example, the latter includes a programmable device with a processor and a memory which has components of code stored which, when executed by the processor, arrange for the latter to then ascertain a position of the virtual tip 104 of the virtual component 102 of the contactless pointer unit on the basis of the captured position and alignment of the real component 101 of the contactless pointer unit. Depending on the embodiment, the position data capture unit 107 and the control unit can be realized as separate components with separate programmable devices, but also as a single component with a common programmable device, for example, within the scope of a navigation system. The control unit 108 is connected to an image output unit 109, for example a screen or else smartglasses, or else a plurality of image output units, which image output unit is configured to display the captured portion of the object, that is, the operating region on the patient 106. The control unit 108 arranges for the image output unit to display the position of the virtual tip in marked fashion in the displayed captured portion of the object. In the shown embodiment, the image output unit 109 is shown as a screen and the control unit adapts the images or image sequences, which are to be displayed, themselves in such a way that it is not only the virtual tip 104 but also the contour of a representation of the virtual component 102 of the contactless pointer unit that is displayed in the image output unit 109.

Figure 2:
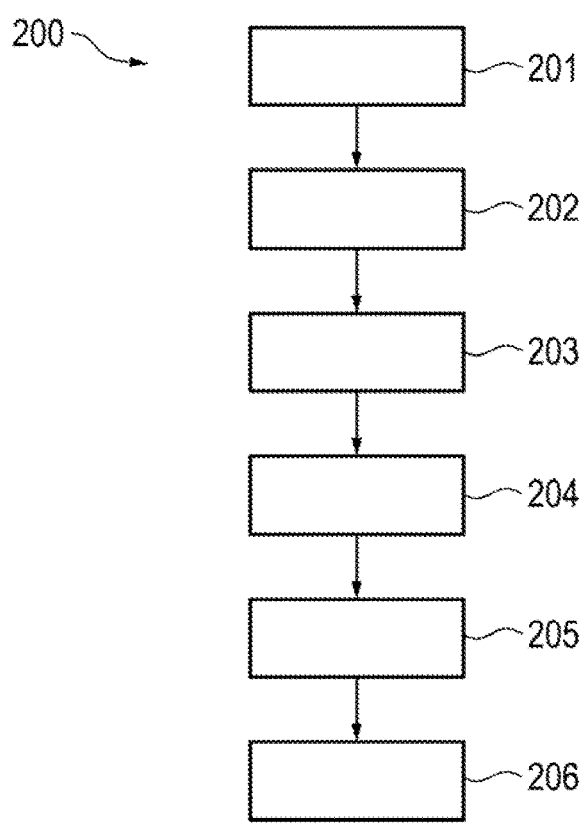
FIG. 2 shows a schematic illustration of an example of a method for operating an optical observation system according to a further embodiment.

FIG. 2 shows a schematic illustration of an example of a method for operating an optical observation system according to a further embodiment. The method 200 for operating an optical observation system such as that shown in FIG. 1, for example, includes a step of capture 201 of at least a portion of an object using an image recording unit of the optical observation system.

Moreover, the method includes an introduction 202 of the real component of a contactless pointer unit into a field of view of an image recording unit which captures at least the portion of the object, the contactless pointer unit having a real component and a virtual component, wherein the real component includes at least one position labeling means and the virtual component includes a virtual tip which is at least intermittently spaced apart from the real component.

Then there is a capture 203 of a position and of an alignment of the real component of the contactless pointer unit using a position data capture unit of the optical observation system.

Furthermore, the method includes a display 204 of the captured portion of the object using an image output unit of the optical observation system.

Additionally, there is an ascertainment 205 of a position of the virtual tip on the basis of the captured position and alignment of the real component of the contactless pointer unit using a control unit of the optical observation system, and a display 206, in marked fashion, of the position of the virtual tip in the displayed captured portion of the object using the image output unit.

Figure 3:
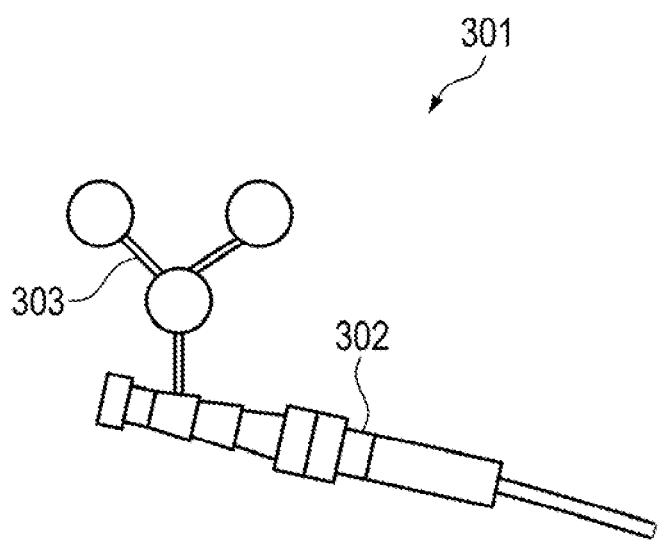
FIG. 3 shows a schematic illustration of a first example of a pointer device for an optical observation system.

FIG. 3 shows a schematic illustration of a first example of a pointer device for an optical observation system. The pointer device 301 is suitable for use as a real component of a contactless pointer unit, for example of the optical observation system shown in FIG. 1. It includes an approximately stick-shaped carrier 302 or handle, on which an optical antenna 303 has been mounted as position labeling means.

Figure 4:
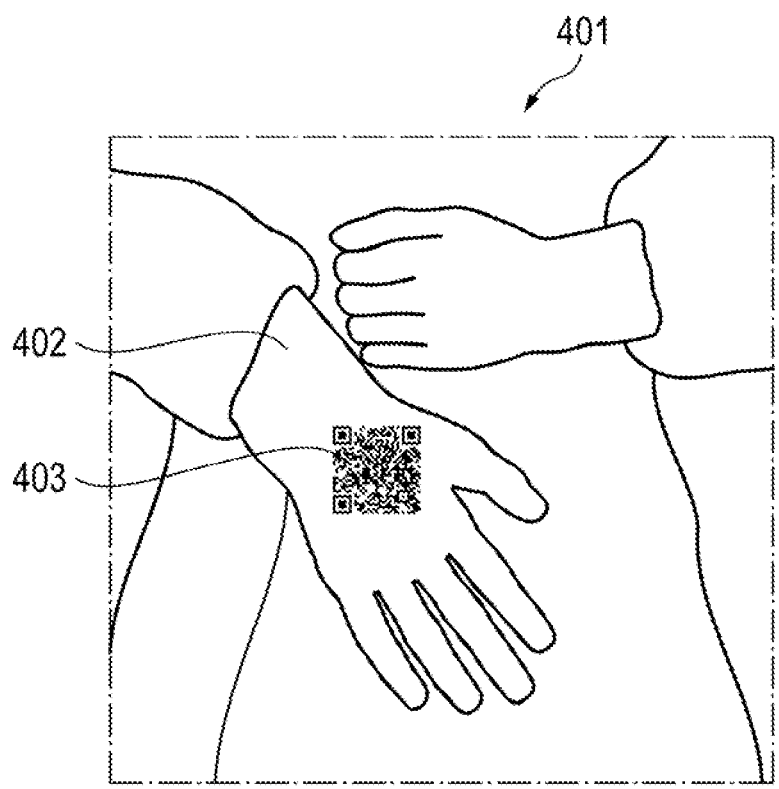
FIG. 4 shows a schematic illustration of a second example of a pointer device for an optical observation system.

FIG. 4 shows a schematic illustration of a second example of a pointer device for an optical observation system. The pointer device 401 is also suitable for use as a real component of a contactless pointer unit, for example of the optical observation system shown in FIG. 1. A surgeon uses a glove as a carrier 402, on which a target mark 403 has been applied, for example printed or adhesively bonded thereon, as position labeling means.

Figure 5:
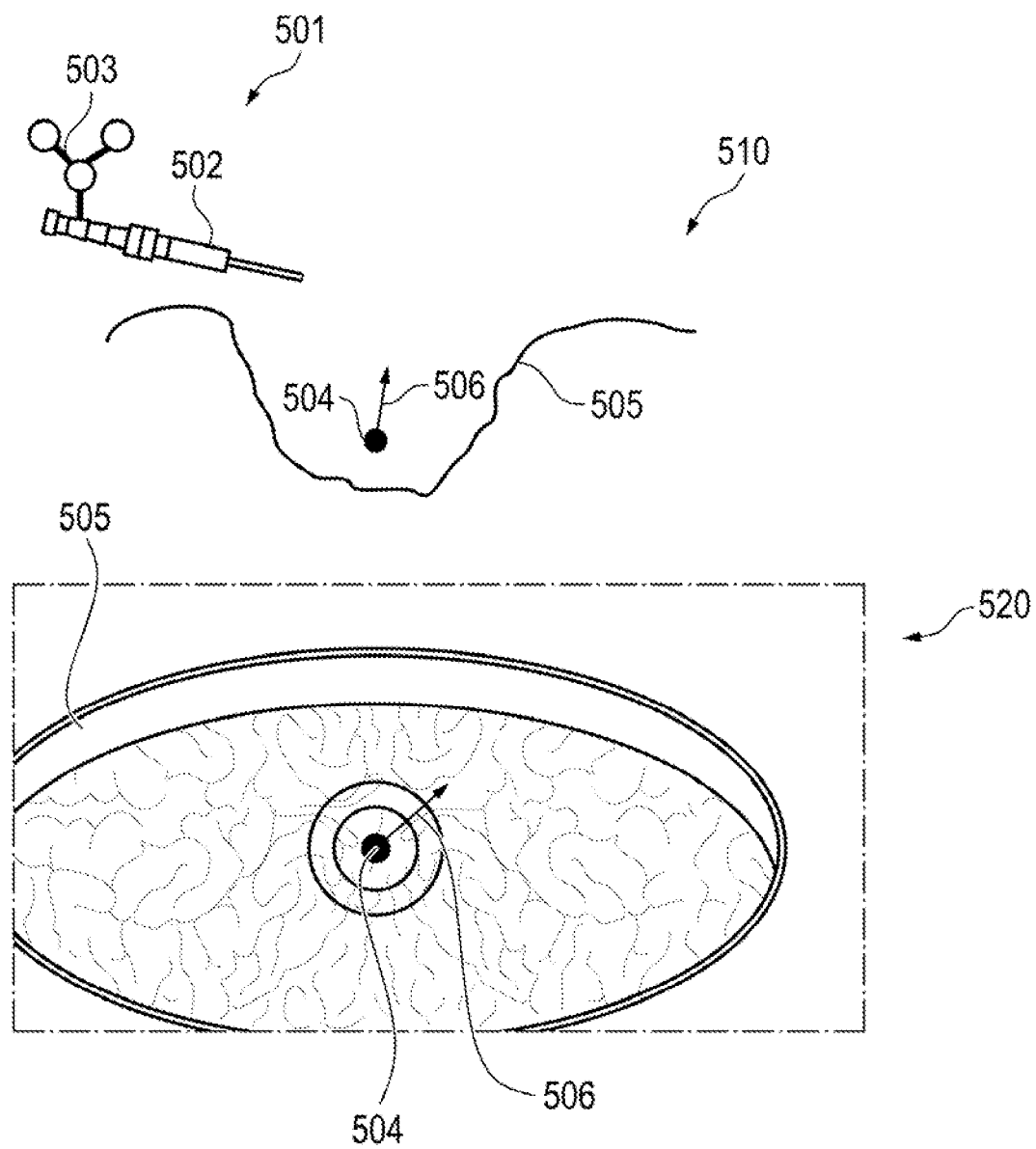
FIG. 5 shows a schematic illustration of a first example of a contactless pointer unit in a site.

FIG. 5 shows a schematic illustration of a first example of a contactless pointer unit in a site, which is illustrated in a first perspective 510 and in a second perspective 520. The approximately stick-shaped carrier 502 of the real component 501 of the contactless pointer unit includes an optical antenna 503 as position labeling means (the use of a target mark, for example, would likewise be possible) and it is moved into the region of a site 505 of a patient. In the shown example, the virtual component of the contactless pointer unit is visualized on the basis of its virtual tip 504, which is represented by a filled circle, the latter having been assigned an arrow 506, the length of which indicates the magnitude of the tilt and the direction indicates the new orientation direction of an image recording unit (not shown) of a robotic surgical microscope as an optical observation system, which is automatically realigned in controlled fashion in accordance with the change in position and alignment of the contactless pointer unit.

Figure 6:
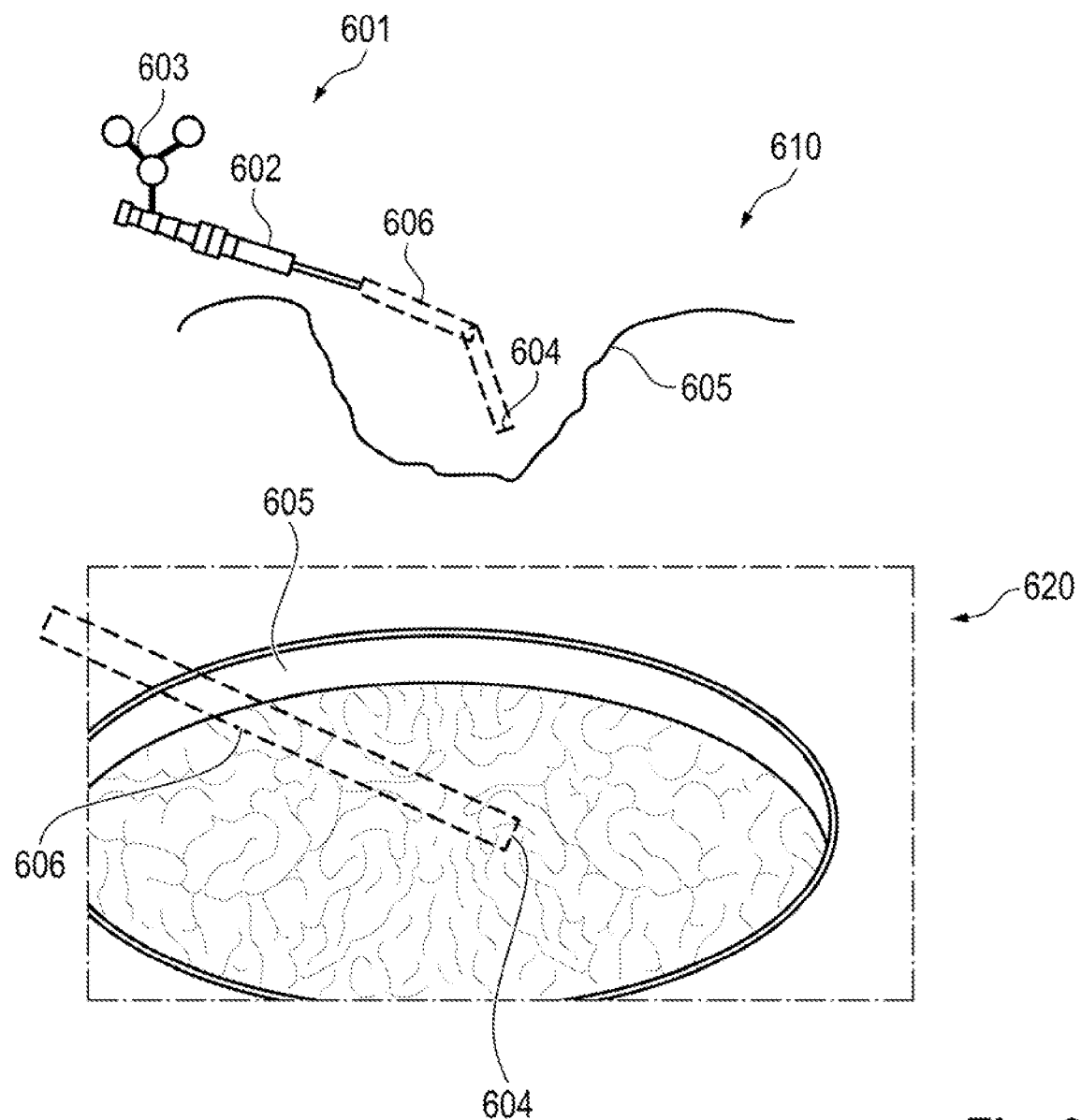
FIG. 6 shows a schematic illustration of a second example of a contactless pointer unit in a site; and, FIG. 7 shows a schematic illustration of a third example of a contactless pointer unit in a site.

FIG. 6 shows a schematic illustration of a second example of a contactless pointer unit in a site, which is illustrated in a first perspective 610 and in a second perspective 620. The approximately stick-shaped carrier 602 of the real component 601 of the contactless pointer unit includes an optical antenna 603 as position labeling means in the shown example and it is moved into the region of a site 605 of a patient. In the shown example, the virtual component 606 of the contactless pointer unit, which includes a virtual tip 604, is represented schematically in dashed fashion on the basis of its contour. Here, too, a change in the alignment and position of the real component 601 of the contactless pointer unit, which is tracked on the basis of the position labeling means, changes the alignment and position of the virtual component 606 and its virtual tip 604. Like in FIG. 5, the latter serves as a virtual tool tip which sets the centration point or focal point for the observation unit, and an align-to-tool function of a control unit of the robotic surgical microscope changes the alignment thereof when the virtual tip 604 changes the centration point.

Figure 7:
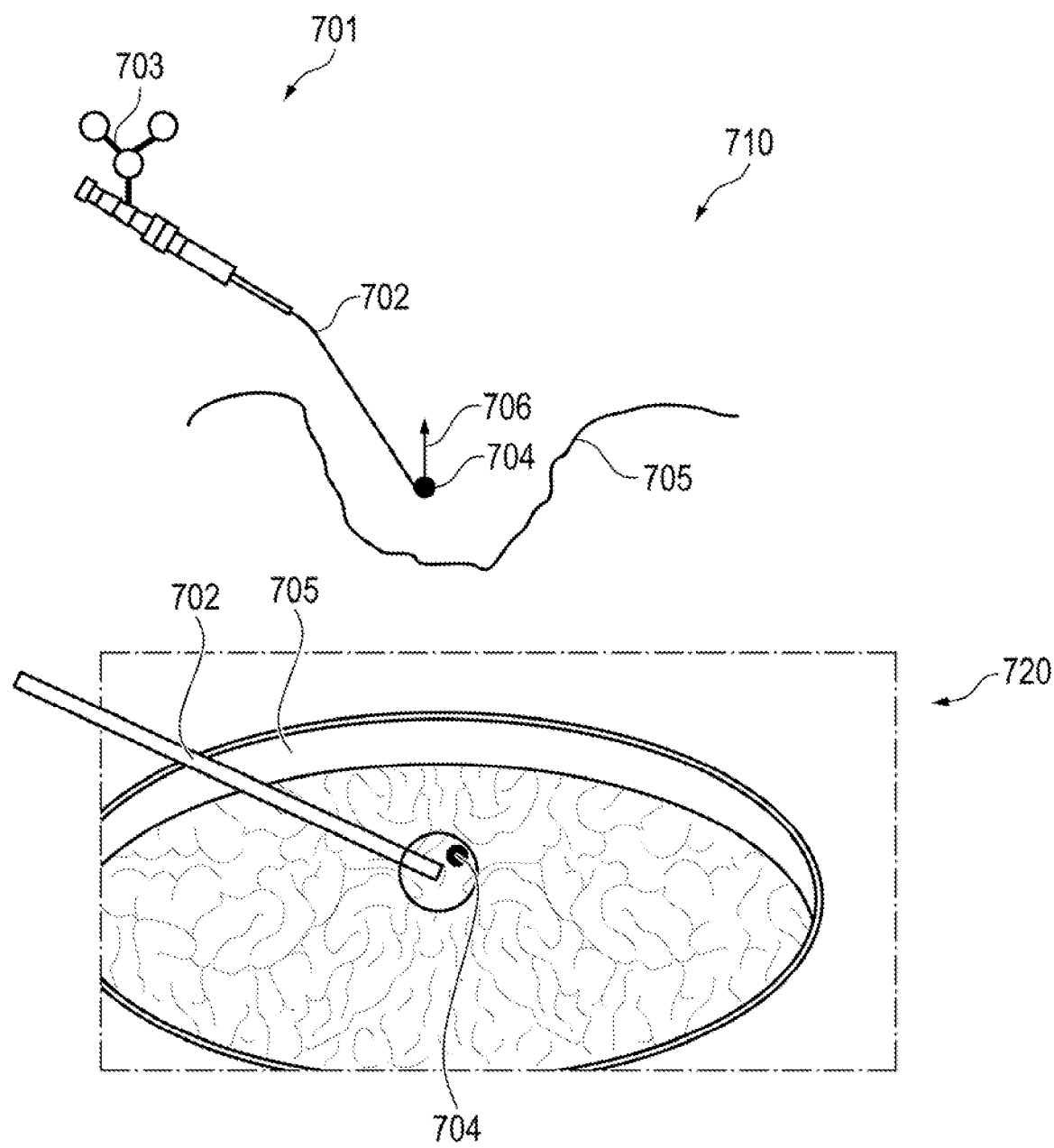

FIG. 7 shows a schematic illustration of a third example of a contactless pointer unit in a site, which is illustrated in a first perspective 710 and in a second perspective 720. The approximately stick-shaped carrier 702 of the real component 701 of the contactless pointer unit includes an optical antenna 703 as position labeling means and it is moved into the region of a site 705 of a patient. In the shown example, the virtual component of the contactless pointer unit is visualized in a manner reduced to the point of a virtual tip 704, which is represented by a filled circle, the latter having been assigned an arrow 706, the length of which indicates the magnitude of the tilt and the direction indicates the new orientation direction of an image recording unit (not shown) of a robotic surgical microscope as an optical observation system, which, automatically, is automatically realigned in controlled fashion in accordance with the change in position and alignment of the contactless pointer unit. The new alignment is implemented by moving the contactless pointer unit in controlled fashion and oriented on the new position of the virtual tip, which is displayed in punctiform fashion. The representation also allows a transmission ratio to be taken into account in order thus to be able to set a new orientation more precisely.

It is to be understood that method steps, although they have been described in a specific ordered sequence, can in part be performed in a different sequence than the one described here. It is also to be understood that specific steps can be performed simultaneously or in succession, once or multiple times, that other steps could be added, or that specific steps described here could be omitted. It is also understood that boundaries between units of the presented system serve to illustrate the functionality of the system and that, in other embodiments, units can be, for example, combined or functionalities can be assigned to other units. Thus, for example, in other embodiments, the image recording unit 105 shown in FIG. 1 can be realized together with the position data capture unit 107 or the position data capture unit 107 can be realized together with the control unit 108 or the image recording unit 105 can be realized together with the position data capture unit 107 and the control unit 108, in each case as a common unit, in order to name but a few examples. In other words: The present descriptions are offered for the purpose of illustrating specific embodiments and should not be interpreted as being a limitation of the subject matter disclosed.

The figures are not necessarily accurate in every detail and to scale and can be presented in enlarged or reduced form for the purpose of better clarity. For this reason, functional details disclosed here should not be understood to be limiting, but merely to be an illustrative basis that gives guidance to a person skilled in this technical field for using the present invention in various ways.

The expression "and/or" used here, when it is used in a series of two or more elements, means that any of the elements listed can be used alone, or any combination of two or more of the elements listed can be used. For example, if a structure is described as containing the components A, B and/or C, the structure can contain A alone; B alone; C alone; A and B in combination; A and C in combination; B and C in combination; or A, B, and C in combination.

The present invention has been described in detail on the basis of embodiments for purposes of explanation. A person skilled in the art recognizes that details that were described with reference to one embodiment can also be used in other embodiments. Therefore, the invention is not intended to be restricted to individual embodiments, but rather only by the appended claims.

It is understood that the foregoing description is that of the preferred embodiments of the invention and that various changes and modifications may be made thereto without departing from the spirit and scope of the invention as defined in the appended claims.

LIST OF REFERENCE SIGNS

100 Optical observation system
101 Real component of a contactless pointer unit
102 Virtual component of a contactless pointer unit
103 Position labeling means
104 Virtual tip
105 Image recording unit
106 Patient
107 Position data capture unit
108 Control unit
109 Image output unit
110 User
200 Method for operating an optical observation system
201 Capturing a portion of an object
202 Introducing the real component of a contactless pointer unit into a field of view of an image recording unit
203 Capturing a position and an alignment of the real component of the contactless pointer unit
204 Displaying the captured portion of the object
205 Ascertaining a position of the virtual tip
206 Displaying, in marked fashion, the position of the virtual tip in the displayed captured portion of the object
301 Pointer device
302 Stick-shaped carrier
303 Optical antenna
401 Pointer device
402 Glove as a carrier
403 Target mark
501 Real component of a contactless pointer unit
502 Stick-shaped carrier
503 Optical antenna
504 Virtual tip
505 Site
506 Arrow
510 First perspective
520 Second perspective
601 Real component of a contactless pointer unit
602 Stick-shaped carrier
603 Optical antenna
604 Virtual tip
605 Site
606 Virtual component of the contactless pointer unit
610 First perspective
620 Second perspective
701 Real component of a contactless pointer unit
702 Stick-shaped carrier
703 Optical antenna
704 Virtual tip
705 Site
706 Arrow
710 First perspective
720 Second perspective

What is claimed is:

1. An optical observation system comprising:
a contactless pointer unit having a real component and a virtual component, wherein the real component includes at least one position labeling device and said virtual component includes a virtual tip which is at least intermittently spaced apart from said real component;
an image recording unit configured to capture at least a portion of an object;
a position data capture unit configured to capture a position and an alignment of said real component of said contactless pointer unit;
an image output unit configured to display the captured portion of the object;
a control unit configured to ascertain a position of the virtual tip on the basis of the captured position and alignment of said real component of said contactless pointer unit and to cause said image output unit to display the position of the virtual tip with a mark in the displayed captured portion of the object;
said virtual component being only defined by the position of the virtual tip thereof in relation to the position of the real component after an initialization phase performed by said control unit; and
said position of said virtual tip being defined by a calculation prescription which is set during said initialization phase wherein at a start, the position of the virtual tip is placed at a defined initial position, and then the real component is initially brought into any desired position and alignment which is then selected as a desired relationship between the virtual tip and the real component and stored as said calculation prescription.

2. The optical observation system of claim 1, wherein said at least one position labeling device includes a target mark.

3. The optical observation system of claim 1, wherein said at least one position labeling device includes an optical antenna.

4. The optical observation system of claim 1, wherein said real component of said contactless pointer unit defines a shape; and, said at least one position labeling device is provided by said shape of said real component of said contactless pointer unit.

5. The optical observation system of claim 1, wherein said control unit is configured to ascertain the position of the virtual tip in accordance with a model of the virtual component of the contactless pointer unit, wherein said model is configurable by a user.

6. The optical observation system of claim 1, wherein said control unit is further configured, on a basis of the ascertained position of said virtual tip, to cause said image output unit to display at least one of selected points and selected regions in the displayed captured portion of the object, in a marked manner and/or with assigned additional information.

7. The optical observation system of claim 6, wherein the additional information comprises topography information of the object at least in a region around the ascertained position of said virtual tip.

8. The optical observation system of claim 1 further comprising a microscope.

9. The optical observation system of claim 8, wherein said microscope is a surgical microscope.

10. The optical observation system of claim 8, wherein said image output unit includes an eyepiece of said microscope and said control device is configured to cause the position of the virtual tip to be a data overlay visible in said eyepiece.

11. The optical observation unit of claim 10, wherein said image output unit includes a screen assigned to said microscope and said control device is configured to arrange for the position of the virtual tip to be an overlay of the portion of the object marked on the screen.

12. The optical observation unit of claim 8, wherein said image output unit includes a screen assigned to said microscope and said control device is configured to arrange for the position of the virtual tip to be an overlay of the portion of the object marked on the screen.

13. The optical observation system of claim 8, wherein said microscope is automatically alignable and includes an alignment control apparatus; and, said control unit is further configured to cause said alignment control apparatus to align said microscope on a basis of the position of said virtual tip.

14. The optical observation system of claim 1, wherein said position data capture unit is configured to continuously update the captured position and alignment of said real component of the contactless pointer unit and said control unit is configured to continuously update the ascertained position of said virtual tip and to cause said image output unit to continuously update said image output.

15. A pointer device for an optical observation system having a contactless pointer unit including a real component and a virtual component, wherein the virtual component includes a virtual tip which is at least intermittently spaced apart from the real component; the optical observation system further having a control unit configured to ascertain a position of the virtual tip on the basis of a captured position and alignment of said real component of said contactless pointer unit and to cause an image output unit to display the position of the virtual tip with a mark;
 the pointer device comprising:
 a pointer device body including a labeling device;
 said pointer device being configured to be the real component of the optical observation system;
 said virtual component being only defined by the position of the virtual tip thereof in relation to the position of the real component after an initialization phase performed by said control unit; and
 said position of said virtual tip being defined by a calculation prescription which is set during said initialization phase wherein at a start, the position of the virtual tip is placed at a defined initial position, and then the real component is initially brought into any desired position and alignment which is then selected as a desired relationship between the virtual tip and the real component and stored as said calculation prescription.

16. The pointer device of claim 15 further comprising:
 at least one of a glove and a ring for a finger of a user;
 said pointer device body including a stick; and,
 said labeling device being mounted on said stick, said glove or said ring.

17. A method for operating an optical observation system, the method comprising:
 capturing at least a portion of an object using an image recording unit of the optical observation system;
 introducing a real component of a contactless pointer unit into a field of view of the image recording unit which captures at least the portion of the object, the contactless pointer unit including the real component and a virtual component, wherein the real component comprises at least one position labeling device and the virtual component comprises a virtual tip which is at least intermittently spaced apart from the real component;
 capturing a position and an alignment of the real component of the contactless pointer unit using a position data capture unit of the optical observation system;
 displaying the captured portion of the object using an image output unit of the optical observation system;
 ascertaining a position of the virtual tip on the basis of the captured position and alignment of the real component of the contactless pointer unit using a control unit of the optical observation system;
 displaying the position of the virtual tip via a mark in the displayed captured portion of the object using the image output unit;
 said virtual component being only defined by the position of the virtual tip thereof in relation to the position of the real component after an initialization phase performed by said control unit; and
 said position of said virtual tip being defined by a calculation prescription which is set during said initialization phase wherein at a start, the position of the virtual tip is placed at a defined initial position, and then the real component is initially brought into any desired position and alignment which is then selected as a desired relationship between the virtual tip and the real component and stored as said calculation prescription.

18. A non-transitory computer readable medium comprising a computer program product comprising computer readable program code for an optical observation system having a contactless pointer unit having a real component and a virtual component, wherein the real component includes at least one position labeling device and said virtual component includes a virtual tip which is at least intermittently spaced apart from said real component, an image recording unit configured to capture at least a portion of an object, a position data capture unit configured to capture a position and an alignment of said real component of said contactless pointer unit, an image output unit configured to display the captured portion of the object, and, a control unit configured to ascertain a position of the virtual tip on the basis of the captured position and alignment of said real component of said contactless pointer unit and to cause said image output unit to display the position of the virtual tip with a mark in the displayed captured portion of the object; the computer program product being configured, when executed by a processor, to cause the optical observation system to carry out the method steps of:
- capturing at least the portion of the object using the image recording unit of the optical observation system;
- introducing the real component of the contactless pointer unit into a field of view of the image recording unit which captures at least the portion of the object, the contactless pointer unit including the real component and the virtual component, wherein the real component comprises the at least one position labeling device and the virtual component comprises the virtual tip which is at least intermittently spaced apart from the real component;
- capturing the position and the alignment of the real component of the contactless pointer unit using the position data capture unit of the optical observation system;
- displaying the captured portion of the object using the image output unit of the optical observation system;
- ascertaining the position of the virtual tip on the basis of the captured position and alignment of the real component of the contactless pointer unit using the control unit of the optical observation system;
- displaying the position of the virtual tip via the mark in the displayed captured portion of the object using the image output unit;
- said virtual component being only defined by the position of the virtual tip thereof in relation to the position of the real component after an initialization phase performed by said control unit; and
- said position of said virtual tip being defined by a calculation prescription which is set during said initialization phase wherein at a start, the position of the virtual tip is placed at a defined initial position, and then the real component is initially brought into any desired position and alignment which is then selected as a desired relationship between the virtual tip and the real component and stored as said calculation prescription.

* * * * *